(12) United States Patent
Eastwood et al.

(10) Patent No.: US 7,972,859 B2
(45) Date of Patent: Jul. 5, 2011

(54) AUTHENTICATION OF INGESTIBLE PRODUCTS USING SACCHARIDES AS MARKERS

(75) Inventors: Ian Eastwood, Rossendale Lancs (GB); Jared Cartwright, York (GB); Erwin Dorland, York (GB); Mark Saw, Rickmansworth (GB)

(73) Assignee: Authentix, Inc., Addison, TX (US)

( * ) Notice: Subject to any disclaimer, the term of this patent is extended or adjusted under 35 U.S.C. 154(b) by 194 days.

(21) Appl. No.: 11/768,766

(22) Filed: Jun. 26, 2007

(65) Prior Publication Data
US 2007/0298502 A1    Dec. 27, 2007

Related U.S. Application Data

(60) Provisional application No. 60/816,812, filed on Jun. 27, 2006.

(51) Int. Cl.
*G01N 33/00* (2006.01)
(52) U.S. Cl. .................. 436/94; 436/20; 436/86; 436/91
(58) Field of Classification Search .................. 436/84, 436/86
See application file for complete search history.

(56) References Cited

U.S. PATENT DOCUMENTS

| | | |
|---|---|---|
| 5,429,952 A | 7/1995 | Garner et al. |
| 5,710,005 A | 1/1998 | Rittenburg |
| 5,776,713 A | 7/1998 | Garner et al. |
| 5,942,444 A | 8/1999 | Rittenburg et al. |
| 6,068,981 A | 5/2000 | Rittenburg et al. |
| 6,140,134 A | 10/2000 | Rittenburg |
| 2005/0239155 A1 | 10/2005 | Alarcon et al. |
| 2006/0035288 A1 | 2/2006 | Green et al. |

FOREIGN PATENT DOCUMENTS

| | | |
|---|---|---|
| EP | 0327163 | 8/1989 |
| EP | 0327163 A2 | 8/1989 |
| WO | WO 00/55609 | 9/2000 |

OTHER PUBLICATIONS

Mackenzie, W.M.; "Counterfeiting and the Diageo Anti-Counterfeiting analytical Strategy" On-line—retrieved from URL: www.nabca.org/media/161_nabca.ppt; May 18, 2007; slides 3 and 4.
Telmer, Patrick G., et al.; "Insights into the Conformational Equilibria of Maltose binding Protein by Analysis of High Affinity Mutants"; The Journal of Biological Chemistry: vol. 278, No. 36, Sep. 5, 2003. pp. 34555-34567.

*Primary Examiner* — Yelena G Gakh
*Assistant Examiner* — David Weisz
(74) *Attorney, Agent, or Firm* — Kelly Kordzik; Matheson Keys Garsson & Kordzik PLLC (57) ABSTRACT

A method of determining authenticity of an ingestible product purportedly from a batch of saccharide-marked ingestible product is provided. The ingestible product is a food, beverage, or pharmaceutical, for example. The method includes identifying a sample of the ingestible product to be tested; and testing the sample for a marked presence of the saccharide using a saccharide-specific binding protein. The ingestible product is not authentic when the testing demonstrates an unexpected change in the marked presence of the saccharide, and the ingestible product is authentic when the testing demonstrates no unexpected change in the marked presence of the saccharide.

12 Claims, 6 Drawing Sheets

Large molecule bound to Gel

FIG. 5

Molecular-eye view of Liquid clean-up

FIG. 6

Molecular-eye view of Liquid clean-up

FIG. 7

Molecular-eye view of Liquid clean-up

AUTHENTICATION OF INGESTIBLE PRODUCTS USING SACCHARIDES AS MARKERS

CROSS-REFERENCE TO RELATED APPLICATIONS

Under 35 U.S.C. §119(e)(1), this application claims the benefit of prior U.S. provisional application 60/816,812, filed Jun. 27, 2006, which is incorporated by reference herein in its entirety.

FIELD OF THE INVENTION

The present invention relates to the field of security and anti-counterfeiting of ingestible products, particularly foods, beverages and pharmaceuticals. The presence of an in-product saccharide marker is verified by interaction with a binding protein having specific binding affinity for the saccharide.

BACKGROUND OF THE INVENTION

The counterfeiting of products is a growing industry that costs companies more than $500 billion annually. In addition to the cost, counterfeit products can be dangerous to consumer health and safety. Ingestion of counterfeit foods, beverages and pharmaceuticals can have tragic consequences. For example, thousands of deaths occur every year due to presence of methanol in counterfeit liquor.

The ingredients of a counterfeit product may be the same as or may be different from those of the genuine product. Even if the ingredients are the same, they may be of inferior quality or may have been adulterated. Product adulteration is when a product is tampered with such as by dilution. An example of such a problem is in the liquor industry where bottles may be refilled or diluted with an inferior product in order to extend the product and to avoid paying taxes.

Efforts exist to authenticate products including use of fluorescently labeled antibodies, addition of light-emissive chemicals to a product, spectroscopic scans against a memory of the authentic brand profile, protein electrophoresis, infrared analysis, gas chromatography, pH, and Raman spectroscopy, among others.

U.S. Patent Publication No. 2006/0035288 to Green et al. relates to methods of detection of counterfeit liquids and foods wherein two or more markers are added to the liquid or food product and presence of the markers is later determined by assay. Use of haptens as marking materials is cited by EP 0 327 163 to Shell Internationale and published Aug. 9, 1989, by U.S. Pat. No. 5,776,713 to Garner et al which issued Jul. 7, 1998, and by U.S. Pat. No. 5,429,952 to Garner et al. which issued Jul. 4, 1995. Gradient lateral flow devices have been described by Rittenburg, J. H. in U.S. Pat. No. 5,710,005 issued Jan. 20, 1998 and in U.S. Pat. No. 6,140,134 issued Oct. 31, 2000. U.S. Pat. No. 6,068,981 issued May 30, 2000 to Rittenburg et al. relates to marking of orally ingested products that pass into a body tissue or fluid in a detectable form. U.S. Pat. No. 5,942,444 issued Aug. 24, 1999 to Rittenburg et al. relates to marking products using a print molecule, print molecule analogue, or molecularly imprinted molecule.

Rapid, cost-effective, and enforceable methods of authenticating an ingestible product are particularly needed in the industry that produces ingestible products.

SUMMARY OF THE INVENTION

In an aspect of the invention, a method of determining authenticity of an ingestible product includes the following steps: identifying an ingestible product to be authenticated; introducing a graded saccharide into a production batch of the ingestible product to form a saccharide-marked batch of product; identifying a sample of an ingestible product purportedly from a batch of the saccharide-marked ingestible product; and testing the sample for a marked presence of the saccharide using a saccharide-specific binding protein. The ingestible product is not authentic when the testing demonstrates an unexpected change in the marked presence of the saccharide, and the ingestible product is authentic when the testing demonstrates no unexpected change in the marked presence of the saccharide.

Implementations of the invention can include one or more of the following features. The saccharide can be a monosaccharide. The monosaccharide may be selected from the group consisting of erythrose, erythrulose, threose, arabinose, lyxose, ribulose, ribose, xylose, xylulose, allose, altrose, fructose, galactose, glucose, gulose, idose, mannose, psicose, sorbose, tagatose, and talose. The saccharide can be a disaccharide or an oligosaccharide. The saccharide can be a derivatized saccharide. The derivatized saccharide may be selected from a group consisting of a deoxy-derivatized saccharide, methylated-derivatized saccharide, acetylated-derivatized saccharide, amine-derivatized saccharide, and phosphate-derivatized saccharide. The saccharide can be a polysaccharide.

A method of determining authenticity of an ingestible product can include packaging the saccharide-marked batch. Introducing the graded saccharide into the production batch may occur just prior to packaging. The testing may be carried out using a lateral flow device. The saccharide may be maltose, and the testing can include use of a maltose binding protein conjugated to an indicator member. The maltose binding protein may be stabilized to storage, heat or alcohol concentration. The testing may be carried out using a dipstick. The testing may include use of an antibody having binding specificity for maltose binding protein. The testing may include field testing using a portable device. The sample can be diluted prior to testing. The sample may be extracted to concentrate the saccharide prior to testing.

A method of determining authenticity of an ingestible product can include introducing a detectable co-marker into the production batch of the product. The detectable co-marker can include a colorant, a vitamin, or an additive. The additive may be selected from the group consisting of m-phenoxybenzoic acid, erythrosine, 4-aminonaphthalene-1-sulphonic acid, amaranth, dofcol brown, 4-amino-1,1-azobenzene-3,4'-disulphonic acid, mordant yellow 7, 4-hydroxy-3-methoxycinnamic acid, 4-hydroxy-3-methoxyphenyl-3-buten-2-one, vanillin, ethyl-4-hydroxy-3-methoxycinnamic acid, 7-amino-4-methylcoumarin, chromotrope FB, ponceau 4R, ponceau S, bieberich scarlet, tropaelin O, curcumin, coniferyl alcohol, hexyl vanillate, and acetovanillone.

In a method of determining authenticity of an ingestible product, the unexpected change in the marked presence of the saccharide can include a substantial absence of the saccharide. The ingestible product may be selected from the group consisting of food, beverage, and pharmaceutical products. The graded saccharide may be selected from the group consisting of food, beverage, and pharmaceutical graded saccharides.

In another aspect of the invention, a method of determining authenticity of an ingestible product includes the following steps: identifying an ingestible product to be authenticated; introducing a first graded saccharide and a second graded saccharide in a known ratio into a production batch of the ingestible product to form a saccharide doubly-marked batch of product; identifying a sample of an ingestible product purportedly from a batch of the saccharide doubly-marked ingestible product; and testing the sample for a marked presence of the first saccharide and of the second saccharide using a first saccharide-specific binding protein and a second-saccharide specific binding protein. The ingestible product is not authentic when the testing demonstrates an unexpected change in the marked presence of the first or second saccharide, or ratio thereof, and the ingestible product is authentic when the testing demonstrates no unexpected change in the marked presence of the first or second saccharide, or ratio thereof. This method is further useful for batch differentiation.

A further aspect of the invention is a gradient lateral flow detection device for assaying a marked presence of a saccharide in a liquid test sample. The device includes a test sample application region; a region reversibly holding a saccharide-specific binding protein immobilized to an indicator member, the saccharide-specific binding protein having binding specificity for the saccharide; and a test region having immobilized thereto either an analogue of the saccharide for which the binding protein has a lower binding affinity as compared to the saccharide, or the saccharide specific to the saccharide-specific binding protein.

An aspect of the invention includes kit comprising, in packaged combination, a carrier adapted to receive a container in close confinement therewith and a first container including a sample-receiving lateral flow solid support. The solid support includes a labeled mobile saccharide binding protein, an immobilized saccharide analogue and an immobilized antibody having binding affinity for the saccharide binding protein. The test kit may include a container having a dilution vial and a diluent. The test kit may further include a container with an ion exchange column or a gel filtration column.

Use of any of the embodiments as described herein in the testing of an ingestible product for authenticity is an aspect of the invention.

Reference numbers of drawings as referred to herein are as follows:
2 Lateral flow device (LFD); lateral flow device system; gradient lateral flow device
10 Saccharide marker; marker
20 Test Sample
22 Ligand containing marker and contaminants
24 Contaminants
30 Indicator member
32 Column
34 Column frit; first frit; second frit
36 Gel
38 Saccharide-specific binding protein; large molecule; marker binding protein
40 Conjugate of saccharide-specific binding protein bound to indicator member
42 Saccharide-specific binding protein bound to saccharide and to indicator member
44 Saccharide-specific binding protein bound to saccharide marker
46 Saccharide-specific binding protein immobilized on gel
47 Saccharide-specific binding protein immobilized on gel and bound to saccharide marker
50 T-line molecule bound to saccharide or saccharide analogue
60 Antibody to saccharide-specific binding protein
70 LFD test sample application position
80 LFD position for holding mobile conjugate 40
90 LFD position for device-bound T-line molecule
100 LFD position for device bound C-line antibody
110 Direction of lateral flow
120 Absorbent pad serving as a sink

DETAILED DESCRIPTION OF THE INVENTION

Embodiments of the present invention provide for authentication of ingestible products using in-product saccharide markers not usually present in the ingestible products together with a saccharide-specific binding protein testing system.

The term "authentication" as used herein, means detecting an unexpected changed presence of an in-product saccharide marker in an ingestible product, which unexpected changed presence may be due to counterfeiting, tampering, dilution, or adulteration, for example.

A "marked presence" of a marker saccharide is any testable property of the saccharide in the production batch of the ingestible product as packaged and may include, for example, the concentration of the saccharide, or a binding affinity constant of a saccharide binding protein having specificity for the saccharide. A "change in a marked presence" is a deviation from an expected "marked presence" as tested using methods set forth herein. For example, a marker may expectedly degrade slowly over time and since this degradation is expected, it is taken into account in the testing procedures for example, by comparison with a sample of the product known to be authentic. Degradation of a saccharide marker may be desirable in a determination of whether a product has been maltreated (e.g. heat stability). In some embodiments, a substantial absence of the saccharide may indicate a change in the marked presence of the saccharide. A sample of the ingestible product to be tested may be the packaged unit itself, for example, when using a dipstick for testing, or may be a sample of product that is removed from a packaged unit of the product.

Ingestible product: An "ingestible product" is a food, beverage, or pharmaceutical product for example, generally taken or administered orally for purposes of digestion, pleasure, or medical need. As used herein, a beverage includes fermented and distilled alcoholic drinks including beer, wine, liquor, and distilled spirits. Authentication of clear and colored spirits such as gin, brandy, whisky, rum, tequila, vodka and flavored liquors, for example, is contemplated in embodiments of the invention.

In-product saccharide marker: An in-product "saccharide marker," as used herein, is a non-antigenic monosaccharide, disaccharide, oligosaccharide, polysaccharide or derivative thereof not normally present in the ingestible product and introduced to a batch volume during production. The ingestible product may contain saccharides other than the saccharide used as a marker due to their natural presence, or their addition as a filler or taste control agent. The presence of such "other saccharides" is taken into account in the choice of saccharide marker used for the authentication testing as set forth herein to eliminate interference from such "other saccharides." In an embodiment of the invention, the saccharide marker is colorless, odorless and sufficiently stable in the ingestible material to be detectable after withstanding conditions of production, packaging, storage, and transport, for example. In another embodiment, the saccharide marker has little or no impact on organoleptic qualities of the ingestible product, i.e., no or little flavor, at the intended use level. For example, sucrose and lactose have a taste threshold of ~10 mM and ~30 mM respectively and, in general, oligomers of sugars have less taste than monomers or dimers.

Saccharides are also referred to as "sugars" or "carbohydrates" and may have a D- or L-stereoisomer configuration, or an α or β anomeric configuration. The saccharide may or may not be an energy source or a metabolite.

A marker monosaccharide may be a 4, 5, 6, 7, 8, or 9 carbon sugar. Exemplary 4-carbon sugars include, for example, erythrose, erythrulose, and threose. Exemplary 5-carbon sugars include, for example, arabinose, lyxose, ribulose, ribose, xylose, and xylulose. Exemplary 6-carbon sugars include, for example, allose, altrose, fructose, galactose, glucose, gulose, idose, mannose, psicose, sorbose, tagatose, and talose.

Derivatives of saccharides are also contemplated herein for use as markers including deoxy-, methylated-, acetylated-, amine- and phosphate-derivatives. For example, rhamnose is 6-deoxy-1-mannose and fucose is a methylated derivative of mannose. Sialic acid N-acetylneuraminate.

Disaccharides and oligosaccharides having up to about 10 sugar residues are contemplated for use herein as markers; maltose, sucrose, lactose, trehalose and cellobiose are examples of a disaccharide. Maltotriose, maltoheptaose, oligomaltose, raffinose, melitose, stachyose and verbascose (tri, tetra and penta respectively) are examples of an oligosaccharide. Polysaccharides include cellulose and amylose, for example.

Further saccharide markers are provided by Table 1 infra.

The marker saccharides can be chemically altered to complement any alterations introduced into the saccharide-specific binding protein. Biochemical assays for saccharides are generally known and, for example, an assay for maltose includes a linked system that converts maltose to glucose, and the glucose is assayed using glucose oxidase or an NAD-linked system.

For a food or beverage product, a graded saccharide is a saccharide that is generally regarded as safe (GRAS). For a pharmaceutical product, a graded saccharide is a pharmaceutical grade saccharide.

An ingestible product may be authenticated by using two or more saccharide markers. For example, a first graded saccharide and a second graded saccharide are introduced in a known ratio into a production batch of the ingestible product to form a saccharide doubly-marked batch of product. In using a double marking procedure, a ratio of the first and second saccharide is provided as a further authentication parameter. Such a method is useful for batch differentiation.

Detectable co-markers may be added to an ingestible product such as those set forth by Garner et al in U.S. Pat. No. 5,429,952, issued Jul. 4, 1995, which patent is incorporated by reference herein in its entirety. The detectable co-marker may be added in combination with a saccharide marker as set forth herein. Use of such a combination adds yet a further parameter for authentication of an ingestible product. Detectable co-markers include colorants, vitamins and additives. Exemplary detectable co-markers include m-phenoxybenzoic acid, erythrosine, 4-aminonaphthalene-1-sulphonic acid, amaranth, dofcol brown, 4-amino-1,1-azobenzene-3,4'-disulphonic acid, mordant yellow 7, 4-hydroxy-3-methoxycinnamic acid, 4-hydroxy-3-methoxyphenyl-3-buten-2-one, vanillin, ethyl-4-hydroxy-3-methoxycinnamic acid, 7-amino-4-methylcoumarin, chromotrope FB, ponceau 4R, ponceau S, bieberich scarlet, tropaelin 0, curcumin, coniferyl alcohol, hexyl vanillate, and acetovanillone. Detection of such co-markers is as set forth by the Garner patent, previously incorporated by reference.

Introduction of an in-product marker to an ingestible product: A marker saccharide is introduced to a production batch of the product at a use level of less than 100 ppm in one embodiment, less than 50 ppm in another embodiment, less than 10 ppm in a third embodiment and less than 1 ppm in a fourth embodiment. In one embodiment, the marker saccharide is introduced to a production batch just prior to packaging. A saccharide marker may be added to an ingestible product together with a flavoring such as caramel or other taste or color modifier. The saccharide marker is made up as a concentrate to facilitate addition to a production batch.

Saccharide binding protein: Detection of a saccharide marker is carried out using a saccharide binding protein having binding affinity and specificity for the saccharide marker. For example, maltose used as a marker is detected using maltose binding protein. The binding of a saccharide and its specific saccharide binding protein means that upon contacting the saccharide and its binding protein, for example, under appropriate conditions of ionic strength, temperature, pH and the like, specific binding will occur to form a stable complex under conditions effective to promote the interaction.

Saccharide binding proteins of embodiments of the invention include binding proteins having binding affinity and specificity for the saccharides provided supra, thereby forming binding pairs, for example, arabinose and arabinose binding protein from *E. coli*, ribose and ribose binding protein from *E. coli*, xylose and xylose binding protein from Thermoanaerobacter, L-xylulose and L-xylulose binding protein, D-allose and D-allose binding protein from *E. coli*, fructose and fructose binding protein, galactose and galactose binding protein, glucose and glucose binding protein, mannose and mannose binding protein, rhamnose and rhamnose binding lectin, fucose and fucose binding protein, maltose and maltose binding protein, maltose and LamB maltose transport protein, sucrose and sucrose binding protein, lactose and lactose binding protein, trehalose/maltose and trehalose/maltose binding protein, and maltotriose and maltotriose binding protein.

Recombinant *E. coli* maltose binding protein is a 41 kDa mature polypeptide of 371 amino acids (the precursor less the signal sequence). Maltose binding protein is used in protein expression to aid the solubility of other recombinant proteins by constructing fusions of the maltose binding protein to a target protein of interest. To facilitate purification, a maltose binding protein construct containing a C-terminal 6× histidine-tag may be used. Purification may also be achieved using a construct overexpressing native maltose binding protein and exploiting its binding affinity to an amylose resin. Binding proteins are produced using bacterial expression systems for good protein yield per volume of production system.

An example of a MBP expression vector is based on the commercially available pET26a vector from Novagen that encodes a C-terminal 6 histidine tag. The maltose binding protein has an N-terminal periplasmic-directing signal sequence that is removed by the bacteria upon entry to the periplasm. The amino acid sequence of MBP is as follows:

```
                                                           SEQ ID NO:1
MKIKTGARIL ALSALTTMMF SASALAKIEE GKLVIWINGD KGYNGLAEVG KKFEKDTGIK    60

VTVEHPDKLE EKFPQVAATG DGPDIIFWAH DRFGGYAQSG LLAEITPDKA FQDKLYPFTW   120

DAVRYNGKLI AYPIAVEALS LIYNKDLLPN PPKTWEEIPA LDKELKAKGK SALMFNLQEP   180

YFTWPLIAAD GGYAFKYENG KYDIKDVGVD NAGAKAGLTF LVDLIKNKHM NADTDYSIAE   240

AAFNKGETAM TINGPWAWSN IDTSKVNYGV TVLPTFKGQP SKPFVGVLSA GINAASPNKE   300

LAKEFLENYL LTDEGLEAVN KDKPLGAVAL KSYEEELAKD PRIAATMENA QKGEIMPNIP   360

QMSAFWYAVR TAVINAASGR QTVDEALKDA QTNSSSVDKL AAALEHHHHH H
```

An *E. coli* BL-21 (DE3) cell line with the pMAL-p2E vector (pET26b-based) was grown in M9 minimal media in a fermenter to a turbidity ($OD_{600}$) of about 0.7 at which time the culture was induced with IPTG to a final concentration of 1 mM. The cells were collected and run through a Continuous Cell Splitter. The soluble fraction was purified by loaded onto a 5 ml Ni-Chelating Hi-Trap column using the ÄKTA Purifier 100 and the "Ni Chelating 5 ml (Direct Load)vl" program. Eluted protein fractions were passed through a S-75 16/60 sepharose gel filtration column and purified MBP was collected.

In addition to efficient purification provided by tags such as the histidine tag cited above, saccharide binding proteins may be engineered to contain short peptide sequences that are epitopes that provide binding sites for commercially available antibodies. This histidine tag cited above is such an epitope. Further epitopic tags that may be engineered into recombinant saccharide binding proteins include FLAGT™, (detected using M1, M2, or M5 monoclonal antibody) HA, c-Myc (detected using anti-c-Myc agarose affinity gel or anti-c-Myc HRP), VSV-G (detected using anti VSV-G polyclonal antibody), V5 and HSV. Antibodies to such epitopes may be obtained from Sigma Aldrich (St. Louis, Mo.) for example.

Maltose binding protein has a Kd for maltose of 1 µM, and is saturated at about 10 µM which is at a level of about 400 ppb. Maltose binding protein also binds maltotriose with a Kd that equates to about 120 ppb. Therefore, a sensitivity of the method herein is about 120 ppb. The affinity of MBP for maltose can be increased (see: Telmer and Shilton (2003) *JBC* 278(36): 34555-34567) to a reported 110 nM.

The saccharide binding protein must be sufficiently stable so as to function under harsh environments that may have an adverse effect on binding affinity. Conditions to which the protein may be exposed include storage for periods of time, lyophilization, humidity, heat, high alcohol levels found in spirits, and acidic, basic, or other conditions present in ingestible products, for example. A further property of saccharide binding proteins used in lateral flow devices is reversible adherence to the detection device.

Saccharide binding protein stability is provided using methods such as obtaining binding proteins from thermophilic organisms, using mutagenesis such as site-directed mutagenesis to enhance binding affinity or selectivity of the protein to a marker, using particularly stable native proteins, or using a "forced evolution" approach such as cultivating an organism in a low concentration of a saccharide energy source and isolating a saccharide-specific binding protein therefrom, the binding protein having binding specificity for the saccharide energy source. For example, a sensitive detection system is obtained by mutagenesis of maltose binding protein to select for those binding proteins having greater binding affinity or, for example, by selecting for a clone grown in continuous culture on very low doses of maltose. To increase binding affinity, specificity or protein stability, amino acids surrounding the binding site are candidates for mutagenesis such as Asn-38, Asp-40, Lys-41, Glu-70, Trp-88, Ala-89, Asp-91, Arg-92, Glu-137, Glu-179, Tyr-181, Phe-284, Met-356, Trp-366 and Arg-370. In addition, amino acids of the interface opposite the ligand binding cleft such as in Telmer and Shilton (2003) Id. are provided for mutagenesis.

An advantage of embodiments of the invention is that no live animal systems are needed for production and development of the system because the binding proteins are produced from bacteria, yeast, cell lines, or plants.

Table 1 provides a listing of saccharides and saccharide binding protein pairs.

TABLE 1

| Saccharide Binding Protein | Saccharide Marker | Saccharide Binding Protein Supplemental Information |
|---|---|---|
| Family 6 CBM (carbohydrate binding proteins) from *Cellvibrio mixtus* | Cellobiose, xylopentaose | |
| CBPA | Cellulose | multidomain, exhibits carboxymethyl cellulase activity |
| CbtA | Cellobiose, cellotriose, cellotetraose | Hyperthermophile protein |
| agpA | mellibiose, raffinose | *Rhizobium meliloti* agpA |
| MPB, MBL | d-mannose, N-acetylglucoasmine, L-Fucose | |
| Annexin V | bisecting glycosaminoglycans | |
| RTB | Galactose | Plant Lectins: Castor Bean |
| GNA | Mannose | Plant Lectins: Snowdrop |
| ConA | Mannose/glucosamine | Plant Lectins: *Canavalis enisformis* |
| DBL | N-acetylgalactosamine | Plant Lectins: *Dolichus biflorus* |

TABLE 1-continued

| Saccharide Binding Protein | Saccharide Marker | Saccharide Binding Protein Supplemental Information |
|---|---|---|
| BL | N-acetylglucosamine | Plant Lectins: Barley |
| MAH | Sialic Acid | Plant Lectins: *Maackia amurensis* |
| ASGP-R | N-acetylgalactosamine Triatennary | hepatocyte receptor |
| Man/GalNAc-4-SO$_4$-receptor (Cell surface receptor) | mannose, fucose etc | transmembrane protein |
| PAPG | glycolipids with galabiose sequence (Glaα4Gal) | bacterial pilus tip protein |
| Verotoxin | Glaα4Galβ4GlcβCer | *Escherichia coli* |
| BabA | Lewis B antigen (Fucα2Galβ3(Fucα4)GlcNAcβ | *H. pylori* |
| SabA | Sialic Acid | *H. pylori* |
| Galectin | β-D-galactopyranoside; lactose, N-acetyllactosamine | |
| VIP36 | high mannose type glycans | MDCK cells |
| SaBP | Sialic acid | |
| XylF | Xylose | |
| ConA | Mannose | |
| Galectin-1, LGALS1 | β-Galactosidase | |
| Aga16B and Aga86E family 6 CBMs | 3,6-anhydro-α-L-galactose-(1,3)-β-Dgalactopyranose(1,4) (Disaccharide Agarose) | |
| ELAM-1 | terminally sialylated lactosylceramides with a variable number of N-acetyllactosamine repeats and at least one fucosylated N-acetylglucosamine residue | endothelial Leukocyte adhesion molecule-1. |
| Serum mannan-binding protein | mannose and N-acetylglucosamine | component of the complement activation pathway |
| FimH Protein | Mannose and it's oligomers | bacterial pilus protein |
| CL-46 | N-acetyl-D-glucosamine and N-acetyl-D-mannosamine | Bovine C-type lectin domain connected to collagen |
| Immulectin-2 | xylose, glucose, lipopolysaccharide and mannan | Insect C-type lectin (requires Ca$^{2+}$) |
| Chitotriosidase (inactivated) | chitin and chitooligosaccharides | Mammalian lectin/chitinase (YM1 and HCgp39/family 18 chitinases |
| Gliolectin | N-acetylglucosamine-terminated *Drosophila* glycans | *Dorsophila* derived lectin involved in the mediation of neuronal cell pathway formation |
| CBP30 | galactose | S-type lectin isolated from baby hamster kidney cells |
| rCBP35 | Galβ1, 4GlcNAcβ1, 3Galβ1, 4-GlcNAc | S-type lectin from mammalian tissue |
| RBP (receptor-binding protein) | Glucopyranosyl saccharides, galactose, and muramyl dipeptide (MurNAc-D-Ala-D-iGln) | from *Lactococcus lactis* The K$_D$'s ~0.26-0.13 μM tested in solution |
| CfCBM2b-1-2 and related proteins | Xylan and multimers | From *C. fimi*. |
| VP8 | Sialic acid containing human cell surface carbohydrates | From a rotavirus strain that infects humans. |
| family 26 CBM (BhCBM26), and a family 25 CBM(BhCBM25) | Starch and α-glucooligosaccharide | *Bacillus halodurans*; the CBM's are from a modular (5 mods) protein maltohexaose-forming amylase |
| CBPA cellulose-binding protein B CBM | Cellulose | *Eubacterium cellulosovens* 5. Modular protein. |
| STL-1 STL-2 | Rhamnose | Trout L-rhamnose binding proteins. |
| L-Xylulose reductase (modified to retain binding and inactivate reductase) | Xylulose | |

Detection of an in-product saccharide marker: Saccharide detection is generally problematic using standard systems due to a low uv-vis absorbance or a need for coupled biochemical assays. In general, detection of an in-product saccharide marker is carried out using a saccharide-specific binding protein and an antibody having specific binding affinity for the binding protein.

A product may be tested by removing a sample for testing or by inserting a dipstick into the product. A sample removed for testing may be diluted, concentrated or treated to remove contaminants prior to testing. Concentration of a test sample and removal of contaminants from a test sample may be accomplished using a Sepharose column as set forth by FIG. 3-FIG. 9, for example. Saccharide specific binding protein 38 having binding affinity for marker 10 is immobilized to Sepharose gel 36 to form immobilized binding protein 46. Immobilized binding protein 46 is placed in column 32 between frits 34 which fix the gel in place and allow diffusion of the marker and contaminants into the Sepharose space where the marker is bound and, therefore, concentrated. Contaminants 24 may be washed out of the column and the isolated and concentrated marker may be eluted using a denaturant or a chaotropic agent. Further analysis of the concentrated saccharide can then be carried out using chemical or biochemical techniques known to one of ordinary skill in the art.

Portable device for authentication: A portable testing device may include a lateral flow device as set forth herein, a dipstick, microtiter plates, beads, particles, membranes, or immunoassay-type devices for small molecules, for example. Suitable materials include those comprising resins, latex, PVC, nylon, nitrocellulose or polyvinylidenedifluoride (PVDF), for example.

A gradient lateral flow device such as described by U.S. Pat. No. 5,710,005, issued Jan. 20, 1998, to Rittenburg, incorporated by reference herein in its entirety, is contemplated herein for use in embodiments of the invention.

Figures 1A, 1B:
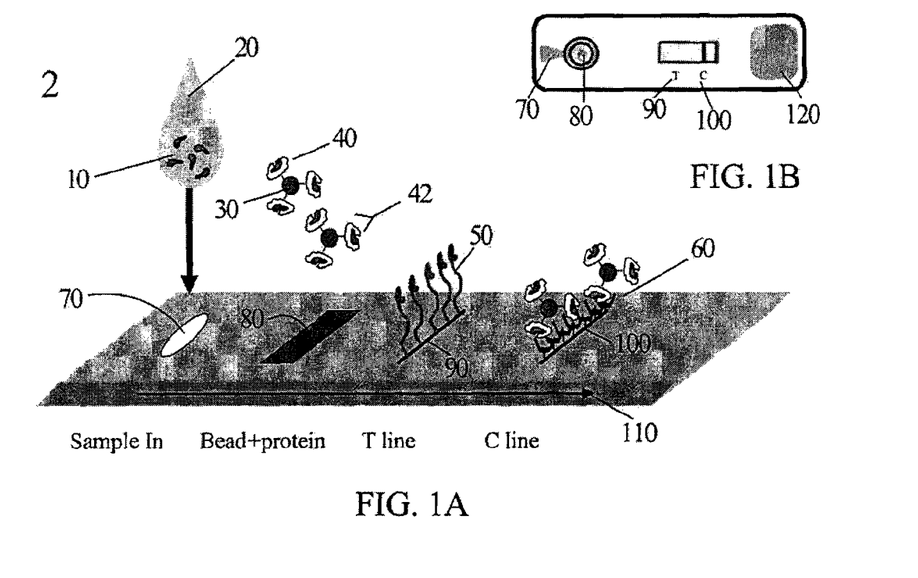
FIG. 1A and FIG. 1B. Lateral flow device system 2 for analyzing presence of marker 10 in test sample 20. Test sample 20 of FIG. 1A contains marker 10 and no binding is seen at T-line 90 since marker binding protein 38 is saturated with marker 10 and is not available for binding at the T-line 90.

FIG. 1A is an illustration of a gradient lateral flow device and FIG. 1B shows a top view of the device. Arrow 110 indicates the direction of lateral flow. The device includes a test sample application position 70 (e.g., an absorbent grade 470 paper from Schleicher and Schuell, Keene, N.H.) to which a test sample is applied. Holding position 80 may be a pad of polyester (e.g., Ahlstrom Filtration, Mt. Holly Springs, Pa.) separated from the test sample application pad by hydrophobic polystyrene, for example, and is for holding saccharide binding protein immobilized to indicator members (e.g., colloidal gold beads). The T-line position 90 is the test zone which, in one embodiment, may be a piece of nitrocellulose membrane (e.g., 15 micron fast flow nitrocellulose; Millipore Corporation, Bedford, Mass.). The T-line position binds and immobilizes a T-line molecule. An optional control position 100 is designated as a C line in FIG. 1A and FIG. 1B, and may also be a piece of nitrocellulose membrane to which is immobilized a C-line molecule. Absorbent pad 120 serves as a sink for excess sample. The absorbent positions of the lateral flow device are oriented and fixed in place along a strip of adhesive-backed plastic, for example.

Figures 2A, 2B:
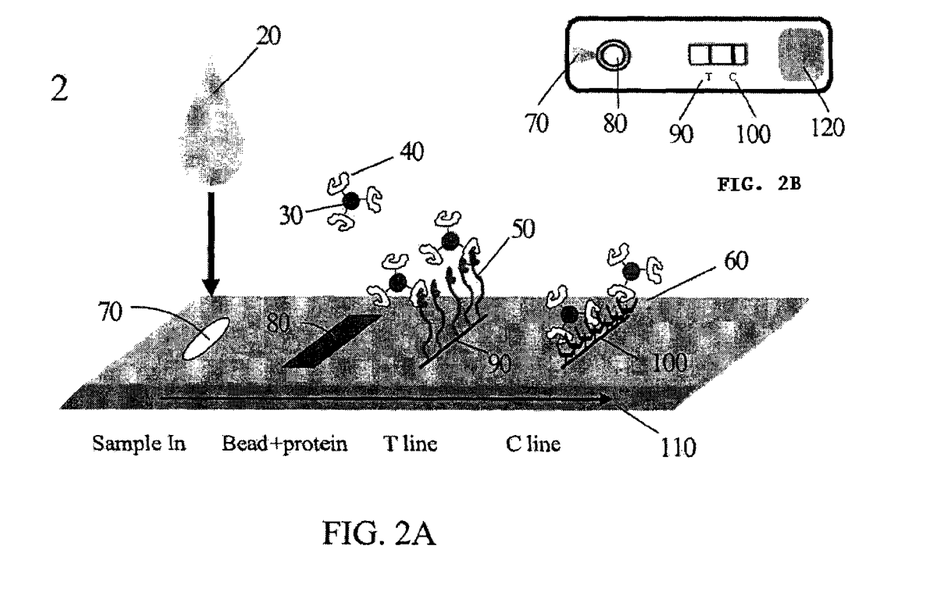
FIG. 2A and FIG. 2B. Lateral flow device system 2 for analyzing presence of marker 10 in test sample 20. Test sample 20 of FIG. 2A does not contain a marker and binding is seen at T-line 90 since marker binding protein 38 is available to bind at T-line 90.
Figure 3:
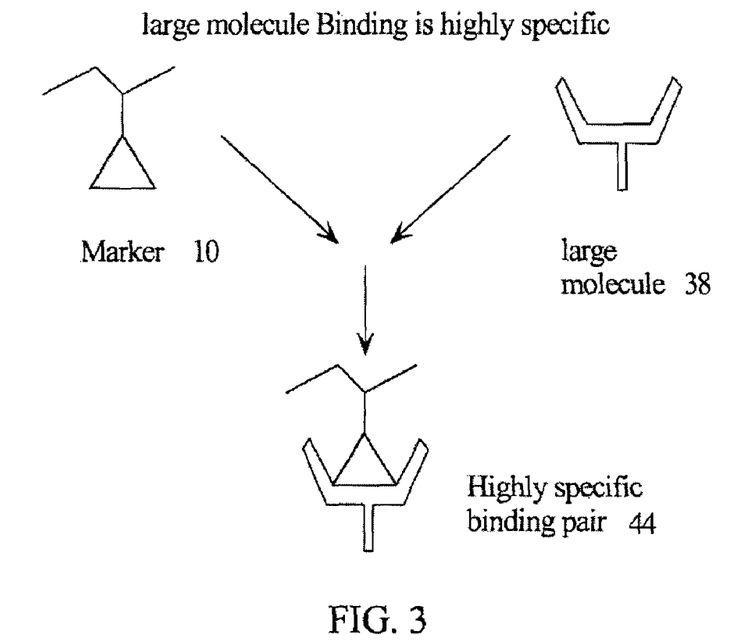
FIG. 3 depicts highly specific binding between saccharide binding protein 38 and saccharide marker 10.
Figure 4:
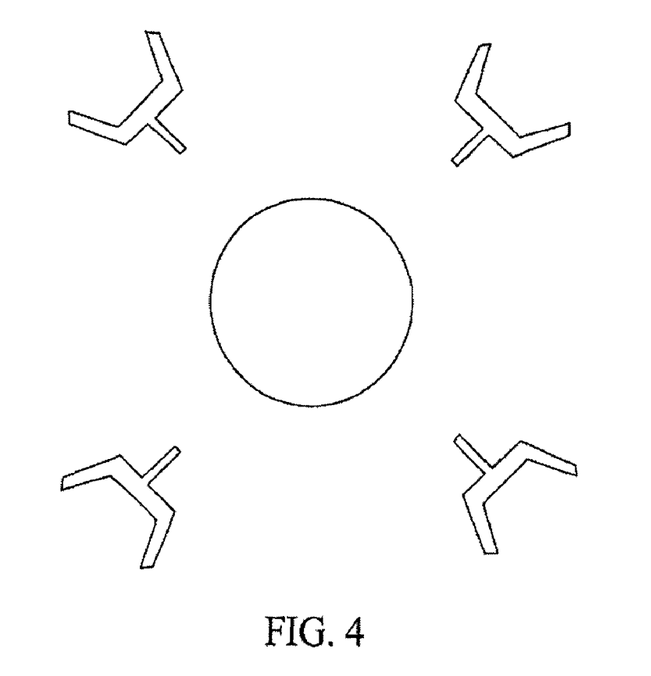
FIG. 4 depicts binding between saccharide binding protein 38 and a gel 36.
Figure 5:
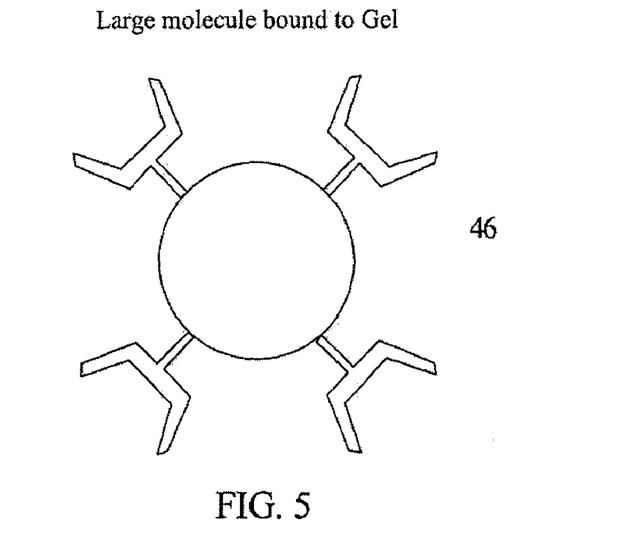
FIG. 5 depicts saccharide binding protein immobilized on a gel.
Figure 6:
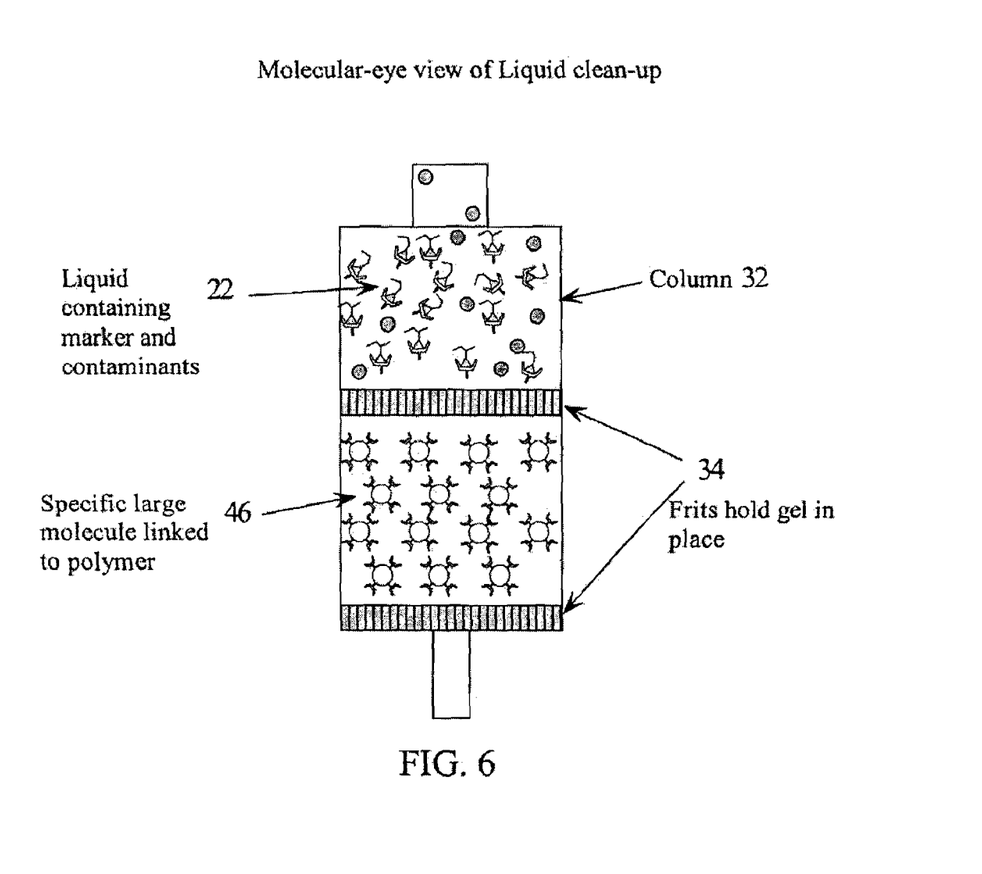
FIG. 6 depicts a process of cleaning a test sample and concentrating a marker present in a test sample using column 32.
Figure 7:
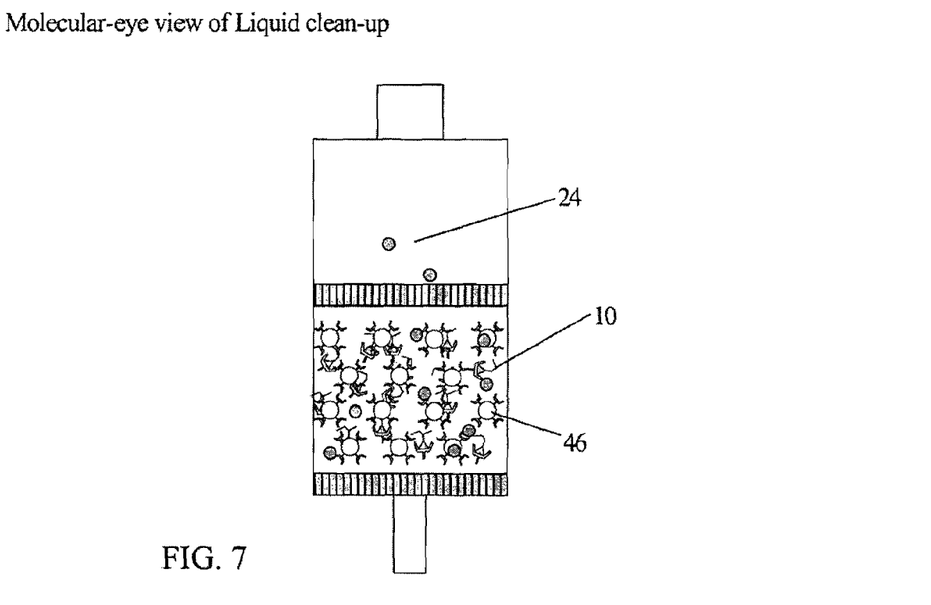
FIG. 7 depicts the process of FIG. 6 where marker and contaminants have nearly all passed through first frit 34.
Figure 8:
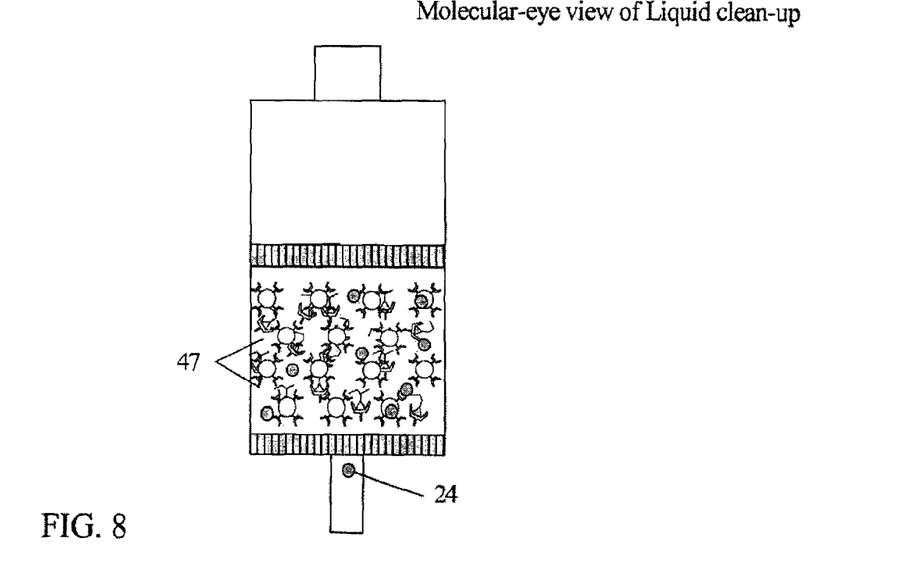
FIG. 8 depicts the process of FIG. 7 where contaminants are being eluted from the column through second frit 34.
Figure 9:
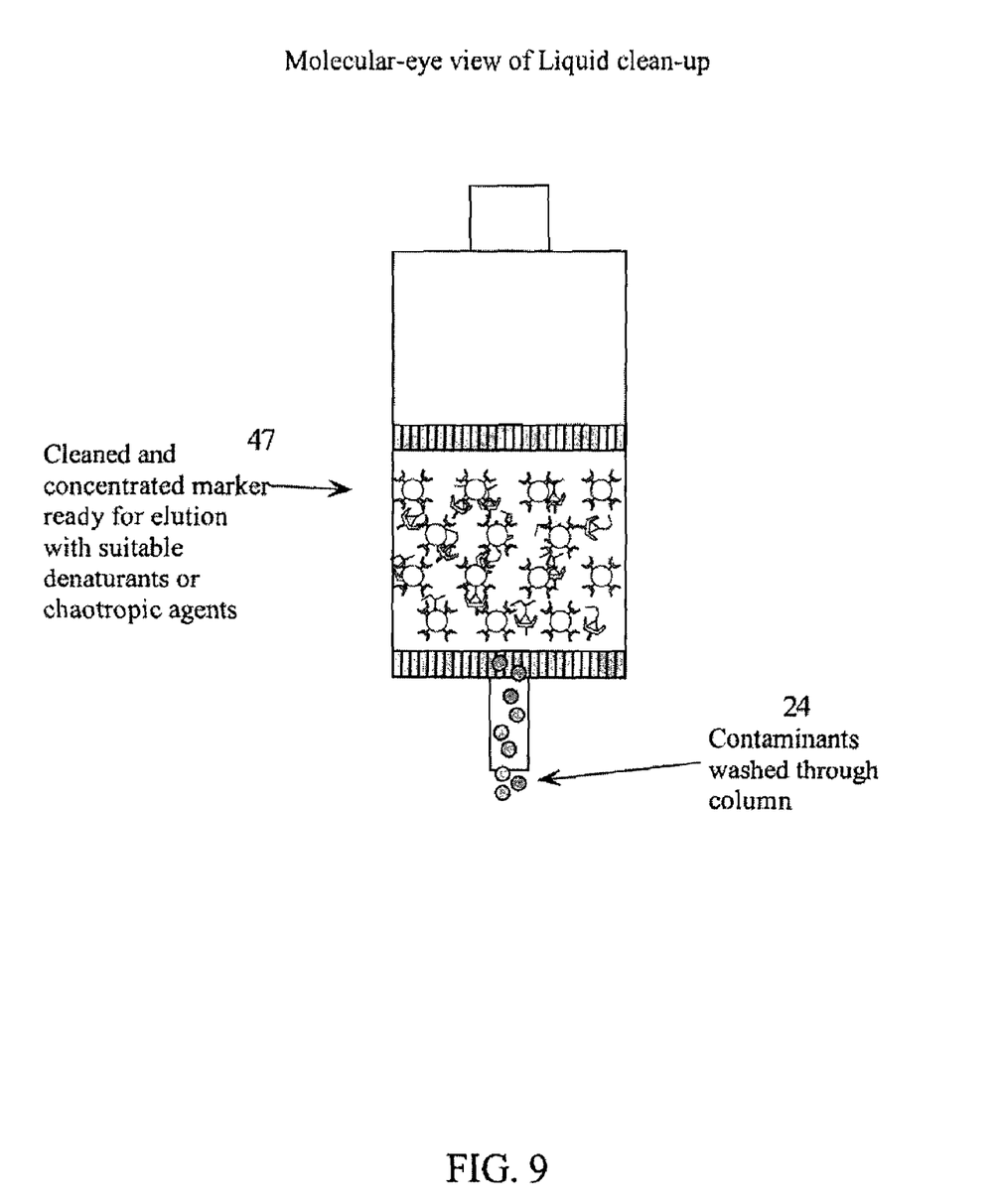
FIG. 9 depicts removal of contaminants 24 and cleaned and concentrated marker ready for elution.

Following analysis of a test sample that lacks authenticity, a visual reaction product is evident in the test position 90 as well as in control zone 100 as shown in FIG. 2A and FIG. 2B and as described below. Following analysis of an authentic test sample as shown in FIG. 1A and FIG. 1B, a visual reaction product is evident only in control zone 100 as described below.

Mobile indicator member and saccharide binding protein: As shown by FIG. 1A and FIG. 1B, in testing for presence of a saccharide marker using a lateral flow device, for example, saccharide binding protein 40 is immobilized to indicator member 30 and together the conjugate is mobile in the direction of lateral flow 110. Examples of an indicator member include colored particles such as colloidal metals (e.g., colloidal gold), carbon, silica, latex (e.g., colored latex beads), dyes, dyed particles, pigments, metal sol particles (e.g., gold or silver metal sol particles), enzymes such as horseradish peroxidase and alkaline phosphatase, fluorophores such as fluorescein and rhodamine, dye-encapsulated liposomes, chemiluminescors, and chromophores. The signaling substance may be a visible substance, such as a colored latex bead, or it may participate in a reaction by which a colored product is produced, or it may be an antibody coupled to a fluorescent or luminescent compound. The reaction product may be visible when viewed with the naked eye, or may be apparent, for example, when exposed to a specialized light source, such as ultraviolet light.

T-line molecule: For a lateral flow device, the "T-line" is a test line, i.e., a region of the device surface having immobilized molecules with a saccharide marker or saccharide marker analogue attached thereto. Saccharide analogues having lower binding affinity for the saccharide binding protein will not displace a marker saccharide from its saccharide binding protein. On the other hand, if the marker saccharide has an unexpected changed presence in the test sample, saccharide binding protein not bound or loosely bound to the test sample will bind to the saccharide analogue on the T line indicating an unexpected changed presence of the marker in the test sample. In a test for maltose marker presence, for example, a T-line molecule may be 'A' resin, a resin bound to amylose. Amylose is bound by maltose binding protein less tightly than is maltose. Therefore, if maltose is absent from a test sample, the maltose binding protein will bind the amylose resin thereby providing a detectable signal at the T-line which is a negative result and indicates the absence of maltose. In one embodiment, the difference of affinity of the T-line molecule as compared to the saccharide marker for the saccharide binding protein will be at least one order of magnitude, e.g., MBP is saturated at a $K_D$ of 10 μM for maltose and has a $K_D$ of >100 μM for amylose.

In a lateral flow device testing system, the concentration of saccharide marker in the test sample that interacts with the saccharide binding protein is determined by the amount of the binding protein or the indicator substance that subsequently becomes associated with the test zone. A reaction within the test zone that produces a measurable reaction product indicates the saccharide marker concentration.

C-line molecule: The C-line or control line molecule is an immobilized antibody having specific binding affinity for the saccharide binding protein. When the saccharide binding protein contains an epitope as cited above, commercially available antibodies having binding specificity and affinity for such epitopes may be used, such as the M1, M2, or M5 monoclonal antibody, anti-HA, anti-c-Myc, anti VSV-G polyclonal antibody, anti-V5 and anti-HSV. Such antibodies may be obtained from Sigma Aldrich (St. Louis, Mo.) for example. Anti-LamB monoclonal antibodies having specificity for maltose transport protein may be used for a maltose lateral flow test device.

The control line molecule will bind the saccharide-specific binding protein/indicator member conjugate and will therefore, give a positive result in a lateral flow device test whether the saccharide marker is or is not present in the test sample. Such a control demonstrates that the assay is working properly.

Kits: A test kit according to an embodiment of the invention includes a dipstick or a lateral flow device as described supra. A kit includes, in one embodiment of the invention, in packaged combination, a carrier means adapted to receive a container means in close confinement therewith and a first container means including a sample-receiving lateral flow solid support which has a labeled mobile saccharide binding protein, an immobilized T-line molecule and an immobilized C-line molecule as set forth supra. In another embodiment of a test kit, a container means provides a dilution vial and/or diluent. In yet another embodiment of a test kit, a container means may include a column for concentrating the sample or for removing contaminant, such as an ion exchange resin or a chromatography medium, such as Sepharose or silica. Printed instructions, either as inserts or as labels, indicating guidelines for use may also be included in the kit.

Example 1

Figure 10:
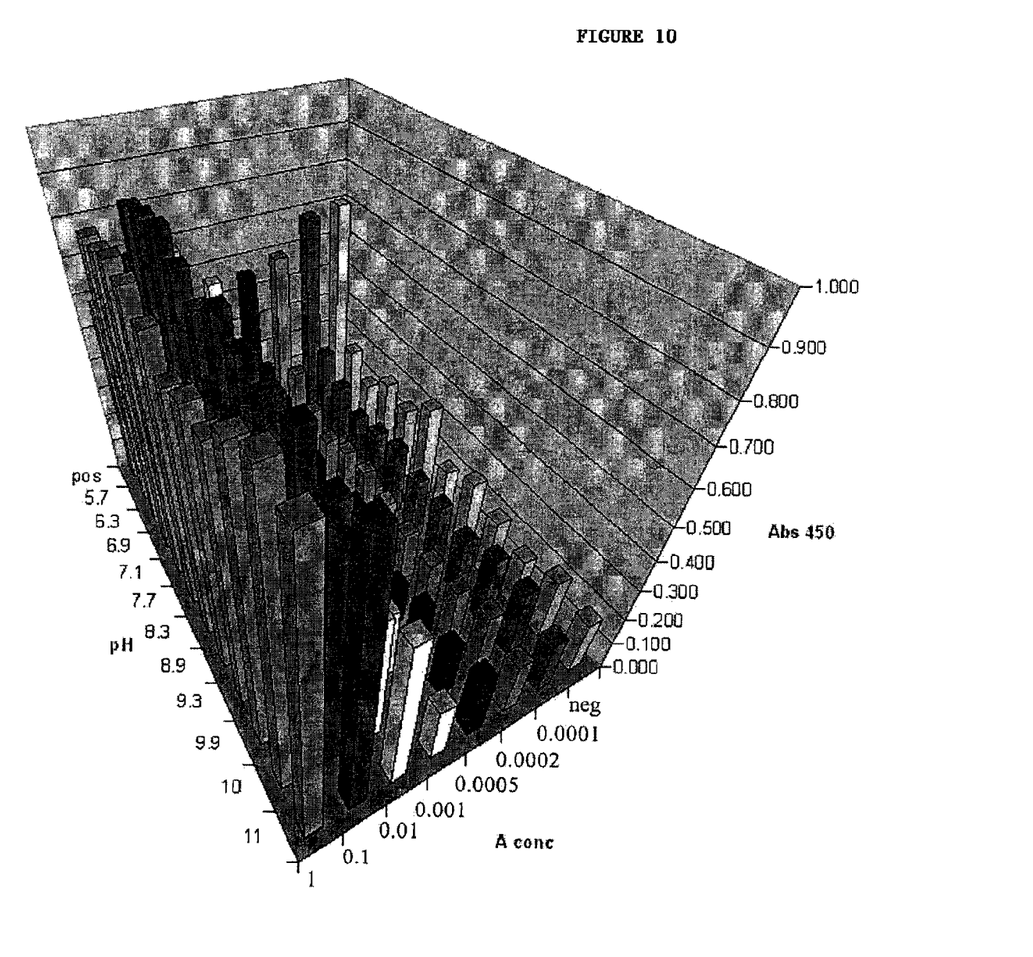
FIG. 10 depicts the extent of amylose binding vs. pH to a MAXISORP™ plate.

This study is to examine the effect of pH on the stability and activity of the MBP protein molecule. FIG. 10 provides an analysis of binding of amylose vs. pH to MAXISORP™ (NUNC, Rochester, N.Y.) using the horseradish peroxidase substrate TMB (Pierce cat #34024). TMB (3,3',5,5' tetramethylbenzidine) is a chromogen that yields a blue color when oxidized with hydrogen peroxide (catalyzed by HRP) with major absorbances at 370 nm and 652 nm. Adding sulfuric or phosphoric acid to stop the reaction changes the product to yellow that absorbs at 450 nm and provides greater sensitivity than the blue product.

Absorbance at 450 nm was measured and the results are provided in Tables 2 and 3.

TABLE 2

| | pos | NaHCO$_3$ buffer, pH | | | | |
|---|---|---|---|---|---|---|
| | | 5.7 | 6.3 | 6.9 | 7.1 | 7.7 |
| 1 | 0.588 | 0.815 | 0.826 | 0.853 | 0.849 | 0.809 |
| 0.1 | 0.693 | 0.861 | 0.879 | 0.896 | 0.855 | 0.817 |
| 0.01 | 0.685 | 0.465 | 0.392 | 0.397 | 0.366 | 0.387 |
| 0.001 | 0.572 | 0.238 | 0.219 | 0.140 | 0.159 | 0.254 |
| 0.0005 | 0.567 | 0.314 | 0.271 | 0.234 | 0.200 | 0.187 |
| 0.0002 | 0.595 | 0.264 | 0.192 | 0.154 | 0.195 | 0.208 |
| 0.0001 | 0.689 | 0.297 | 0.243 | 0.199 | 0.217 | 0.242 |
| Neg | 0.706 | 0.279 | 0.212 | 0.285 | 0.263 | 0.340 |

TABLE 3

| | Pos | Na$_2$CO$_3$ buffer, pH | | | | | |
|---|---|---|---|---|---|---|---|
| | | 8.3 | 8.9 | 9.3 | 9.9 | 10 | 11 |
| 1 | 0.588 | 0.748 | 0.787 | 0.788 | 0.868 | 0.918 | 0.908 |
| 0.1 | 0.693 | 0.870 | 0.847 | 0.828 | 0.849 | 0.793 | 0.845 |
| 0.01 | 0.685 | 0.440 | 0.502 | 0.438 | 0.452 | 0.432 | 0.512 |
| 0.001 | 0.572 | 0.216 | 0.248 | 0.179 | 0.241 | 0.160 | 0.193 |
| 0.0005 | 0.567 | 0.233 | 0.175 | 0.152 | 0.192 | 0.183 | 0.215 |
| 0.0002 | 0.595 | 0.181 | 0.170 | 0.169 | 0.182 | 0.224 | 0.183 |
| 0.0001 | 0.689 | 0.215 | 0.215 | 0.196 | 0.235 | 0.237 | 0.185 |
| Neg | 0.706 | 0.200 | 0.245 | 0.206 | 0.172 | 0.210 | 0.182 |

A negative control lacking amylose and blocked with a blocking solution (PBS+dried low-fat milk powder, Marvel) was also carried out. As shown by FIG. 10, MBP is stable over a relatively wide range of pH, i.e., pH 6.0-pH 9.5. Therefore, MBP is expected to be stable and active in test samples having a pH within such a range. For any test samples outside of such a range, dilution with a buffered solution is carried out.

Further methods of detection and quantification can be obtained using mass spectrometry, ELISA methods, column binding inhibition studies or HPLC, for example.

Example 2

Further studies have shown that 50 μM of the saccharide marker maltose is sufficient to interfere with 90% of the binding of MBP with amylose; and at 5 mM maltose, the binding of MBP to amylose is inhibited to 95% in <20% laboratory ethanol. Vodka, for example, has a concentration of about 20% ethanol when diluted 1:1 with buffer. ELISA studies indicate that 50% inhibition of the amylose-MBP-binding can be induced with 5-10 μM of maltose.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A method of determining authenticity of an ingestible product selected from the group consisting of food and beverage, comprising:

(a) identifying an ingestible product to be authenticated;

(b) introducing a graded saccharide into a production batch of the ingestible product to form a saccharide-marked batch of the ingestible product;

(c) identifying a sample of an ingestible product purportedly from the saccharide-marked batch of product; and
(d) testing the sample for a marked presence of the saccharide using a saccharide-specific binding protein, wherein the saccharide-specific binding protein is stabilized to storage, heat, or alcohol concentration, and wherein
　(i) the ingestible product is not authentic when the testing demonstrates an unexpected change in the marked presence of the saccharide, and
　(ii) the ingestible product is authentic when the testing demonstrates no unexpected change in the marked presence of the saccharide, wherein the saccharide is maltose and the saccharide specific binding protein is a maltose binding protein.

2. The method of claim 1, further comprising packaging the saccharide-marked batch, wherein introducing the graded saccharide into the production batch occurs just prior to packaging.

3. The method of claim 1, wherein the testing is carried out using a lateral flow device.

4. The method of claim 3, wherein the testing comprises use of the maltose binding protein conjugated to an indicator member.

5. The method of claim 1, wherein the testing is carried out using a dipstick.

6. The method of claim 5, wherein the testing comprises use of an antibody having binding specificity for maltose binding protein.

7. The method of claim 1, wherein the testing is field testing using a portable device.

8. The method of claim 1, wherein the sample is diluted prior to testing.

9. The method of claim 1, wherein the sample is extracted to concentrate the saccharide prior to testing.

10. The method of claim 1, further comprising introducing a detectable co-marker into the production batch of the product.

11. The method of claim 10, wherein the detectable co-marker comprises a colorant, a vitamin, or an additive, wherein the additive is selected from the group consisting of m-phenoxybenzoic acid, erythrosine, 4-aminonaphthalene-1-sulphonic acid, amaranth, dofcol brown, 4-amino-1,1'-azobenzene-3,4'-disulphonic acid, mordant yellow 7, 4-hydroxy-3-methoxycinnamic acid, 4-hydroxy-3-methoxyphenyl-3-buten-2-one, vanillin, ethyl-4-hydroxy-3-methoxycinnamic acid, 7-amino-4-methylcoumarin, chromotrope FB, ponceau 4R, ponceau S, bieberich scarlet, tropaelin o, curcumin, coniferyl alcohol, hexyl vanillate, and acetovanillone.

12. The method of claim 1, wherein the unexpected change in the marked presence of the saccharide comprises a substantial absence of the saccharide.

* * * * *

UNITED STATES PATENT AND TRADEMARK OFFICE
CERTIFICATE OF CORRECTION

| | | |
|---|---|---|
| PATENT NO. | : 7,972,859 B2 | Page 1 of 1 |
| APPLICATION NO. | : 11/768766 | |
| DATED | : July 5, 2011 | |
| INVENTOR(S) | : Ian Eastwood et al. | |

It is certified that error appears in the above-identified patent and that said Letters Patent is hereby corrected as shown below:

Column 1, Line 49, replace "Garner et al which" with -- Garner et al. which --
Column 5, Line 62, replace "Garner et al in" with -- Garner et al. in --
Column 7, Line 31, replace "FLAGT™" with -- FLAG™ --
Column 18, Line 21, replace "tropaelin o, curcumin," with -- tropaelin O, curcumin, --

Signed and Sealed this
Fifth Day of June, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 411
<212> TYPE: PRT
<213> ORGANISM: Escherichia coli

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

-continued

```
Leu Val Ile Trp Ile Asn Gly Asp Lys Gly Tyr Asn Gly Leu Ala Glu
            35              40                  45
Val Gly Lys Lys Phe Glu Lys Asp Thr Gly Ile Lys Val Thr Val Glu
    50              55                  60
His Pro Asp Lys Leu Glu Lys Phe Pro Gln Val Ala Ala Thr Gly
65              70              75                  80
Asp Gly Pro Asp Ile Ile Phe Trp Ala His Asp Arg Phe Gly Gly Tyr
                85              90                  95
Ala Gln Ser Gly Leu Leu Ala Glu Ile Thr Pro Asp Lys Ala Phe Gln
                100             105             110
Asp Lys Leu Tyr Pro Phe Thr Trp Asp Ala Val Arg Tyr Asn Gly Lys
            115             120             125
Leu Ile Ala Tyr Pro Ile Ala Val Glu Ala Leu Ser Leu Ile Tyr Asn
            130             135             140
Lys Asp Leu Leu Pro Asn Pro Pro Lys Thr Trp Glu Glu Ile Pro Ala
145             150             155             160
Leu Asp Lys Glu Leu Lys Ala Lys Gly Lys Ser Ala Leu Met Phe Asn
                165             170             175
Leu Gln Glu Pro Tyr Phe Thr Trp Pro Leu Ile Ala Ala Asp Gly Gly
                180             185             190
Tyr Ala Phe Lys Tyr Glu Asn Gly Lys Tyr Asp Ile Lys Asp Val Gly
                195             200             205
Val Asp Asn Ala Gly Ala Lys Ala Gly Leu Thr Phe Leu Val Asp Leu
        210             215             220
Ile Lys Asn Lys His Met Asn Ala Asp Thr Asp Tyr Ser Ile Ala Glu
225                 230             235             240
Ala Ala Phe Asn Lys Gly Glu Thr Ala Met Thr Ile Asn Gly Pro Trp
                245             250             255
Ala Trp Ser Asn Ile Asp Thr Ser Lys Val Asn Tyr Gly Val Thr Val
                260             265             270
Leu Pro Thr Phe Lys Gly Gln Pro Ser Lys Pro Phe Val Gly Val Leu
            275             280             285
Ser Ala Gly Ile Asn Ala Ala Ser Pro Asn Lys Glu Leu Ala Lys Glu
            290             295             300
Phe Leu Glu Asn Tyr Leu Leu Thr Asp Glu Gly Leu Glu Ala Val Asn
305             310             315             320
Lys Asp Lys Pro Leu Gly Ala Val Ala Leu Lys Ser Tyr Glu Glu Glu
                325             330             335
Leu Ala Lys Asp Pro Arg Ile Ala Ala Thr Met Glu Asn Ala Gln Lys
                340             345             350
Gly Glu Ile Met Pro Asn Ile Pro Gln Met Ser Ala Phe Trp Tyr Ala
                355             360             365
Val Arg Thr Ala Val Ile Asn Ala Ala Ser Gly Arg Gln Thr Val Asp
    370             375             380
Glu Ala Leu Lys Asp Ala Gln Thr Asn Ser Ser Ser Val Asp Lys Leu
385             390             395             400
Ala Ala Ala Leu Glu His His His His His His
                405             410
```